(12) United States Patent
Basak et al.

(10) Patent No.: US 11,509,709 B1
(45) Date of Patent: Nov. 22, 2022

(54) PROVIDING ACCESS TO ENCRYPTED INSIGHTS USING ANONYMOUS INSIGHT RECORDS

(71) Applicant: FortifID, Inc., San Jose, CA (US)

(72) Inventors: Anirban Basak, San Jose, CA (US); Thomas P. Hardjono, Winchester, MA (US)

(73) Assignee: FortifID, Inc., San Jose, CA (US)

( * ) Notice: Subject to any disclaimer, the term of this patent is extended or adjusted under 35 U.S.C. 154(b) by 0 days.

(21) Appl. No.: 17/405,578

(22) Filed: Aug. 18, 2021

(51) Int. Cl.
```
H04L 67/06      (2022.01)
H04L 67/1097    (2022.01)
G16H 10/60      (2018.01)
G06F 7/58       (2006.01)
H04L 9/32       (2006.01)
H04L 9/00       (2022.01)
```

(52) U.S. Cl.
CPC ............ H04L 67/06 (2013.01); G06F 7/588 (2013.01); G16H 10/60 (2018.01); H04L 9/3247 (2013.01); H04L 67/1097 (2013.01); H04L 9/50 (2022.05)

(58) Field of Classification Search
CPC . H04L 9/32; H04L 9/0643; H04L 9/50; H04L 9/3239; H04L 9/3236; H04L 67/1097; H04L 67/12; G06F 16/278; G06F 16/27
See application file for complete search history.

(56) References Cited

U.S. PATENT DOCUMENTS

| | | | | |
|---|---|---|---|---|
| 11,037,227 B1* | 6/2021 | Padilha | ................. | G06F 21/602 |
| 2019/0012466 A1* | 1/2019 | Ricotta | ................. | H04L 63/102 |
| 2019/0020629 A1* | 1/2019 | Baird, III | .............. | H04L 9/3066 |
| 2019/0036887 A1* | 1/2019 | Miller | ....................... | G07C 9/20 |
| 2019/0173854 A1* | 6/2019 | Beck | ..................... | H04L 63/123 |
| 2019/0363874 A1* | 11/2019 | Shirley | ................. | H04L 9/3239 |
| 2019/0370250 A1* | 12/2019 | Tipton | .............. | G06Q 20/3829 |
| 2020/0026699 A1* | 1/2020 | Zhang | ................... | H04L 9/0643 |
| 2020/0074853 A1* | 3/2020 | Miller | .................... | H04W 4/02 |
| 2020/0076884 A1* | 3/2020 | Li | ......................... | H04L 9/0637 |
| 2020/0159889 A1* | 5/2020 | Chui | ..................... | G06F 21/105 |
| 2020/0202038 A1* | 6/2020 | Zhang | ................... | G16B 20/20 |
| 2020/0389309 A1* | 12/2020 | Ricotta | ................. | H04L 9/3239 |
| 2021/0357893 A1* | 11/2021 | Kang | ................. | G06Q 20/0457 |
| 2021/0392003 A1* | 12/2021 | Law | ........................ | H04L 9/085 |
| 2022/0014367 A1* | 1/2022 | Law | .......................... | H04L 9/50 |
| 2022/0027319 A1* | 1/2022 | Narayanam | ........... | H04L 9/3239 |

\* cited by examiner

*Primary Examiner* — Tae K Kim (74) *Attorney, Agent, or Firm* — Nicholson De Vos Webster & Elliott LLP (57) ABSTRACT

Techniques are described for algorithmic confidential computing on personal data and to an insights provider providing access to personal data using limited-use anonymous insights records stored on a blockchain. To enable service providers and other queriers to obtain such insights information in a secure manner, an insights provider creates an anonymous insights record that is recorded on a blockchain responsive a request from a subject indicating that the subject desires to share one or more items of insights information. An anonymous insights record contains a single-use (or limited number of use) random number that is used by the insights provider to index the data in a shards index database for the relevant shards of the insights data file. These multiple segments can then be stored across multiple separate repositories using a decentralized file storage service.

20 Claims, 5 Drawing Sheets

PROVIDING ACCESS TO ENCRYPTED INSIGHTS USING ANONYMOUS INSIGHT RECORDS

BACKGROUND

Many existing products and services seek to obtain consent from consumers related to various uses of their private data. When insight information is sought regarding an individual in the context of a transaction related to that individual, privacy of the individual can be compromised by the intentional or inadvertent leaking of such private information. For example, when a person seeks to obtain a mortgage or other type of financial loan, a loan provider typically performs a risk analysis process that requires the person to provide items of private information such as a Social Security Number (SSN). This information is then typically used by the loan provider to query external data providers (e.g., banks, credit card providers, etc.) to obtain additional data about the individual possessed by the data providers. In many cases, the private information provided by the individual is retained afterwards by the service provider even though the service provider does not need to possess the data beyond the completion of the requested transaction. The transmission, use, and retention of such private data by various service providers and data providers causes individuals' private data to be susceptible to many types of undesired uses.

BRIEF DESCRIPTION OF DRAWINGS

Various embodiments in accordance with the present disclosure will be described with reference to the drawings, in which.

DETAILED DESCRIPTION

The present disclosure relates to methods, apparatus, systems, and non-transitory computer-readable storage media for algorithmic confidential computing on personal data and to an insights provider providing access to personal data using limited-use anonymous insights records stored on a blockchain. When a person (or "subject") seeks services from a service provider (e.g., a loan from a loan provider), the service provider often obtains and uses additional information and insights about the subject to make an informed risk analysis decision about whether to provide the services and on what terms. To ensure that the data obtained by the service provider provides accurate information about the subject, the service provider seeks to obtain the data from trusted data providers. However, data providers increasingly are unable to provide subjects' data to other service providers due to privacy regulations and other restrictions in various jurisdictions. Another concern involves the service provider retaining subjects' data obtained from data providers beyond a duration of time that subjects initially consented to its use. According to examples described herein, the aforementioned challenges, among others, are addressed by techniques that enable an insights provider to provide secure access to users' personal data using anonymous insights records stored on a blockchain. Among other benefits described herein, these anonymous insights records are associated with random subject identifiers that can be used a limited number of times, thereby protecting subjects' personal information from undesirable accesses by external entities and other potential misuses.

Figure 1:
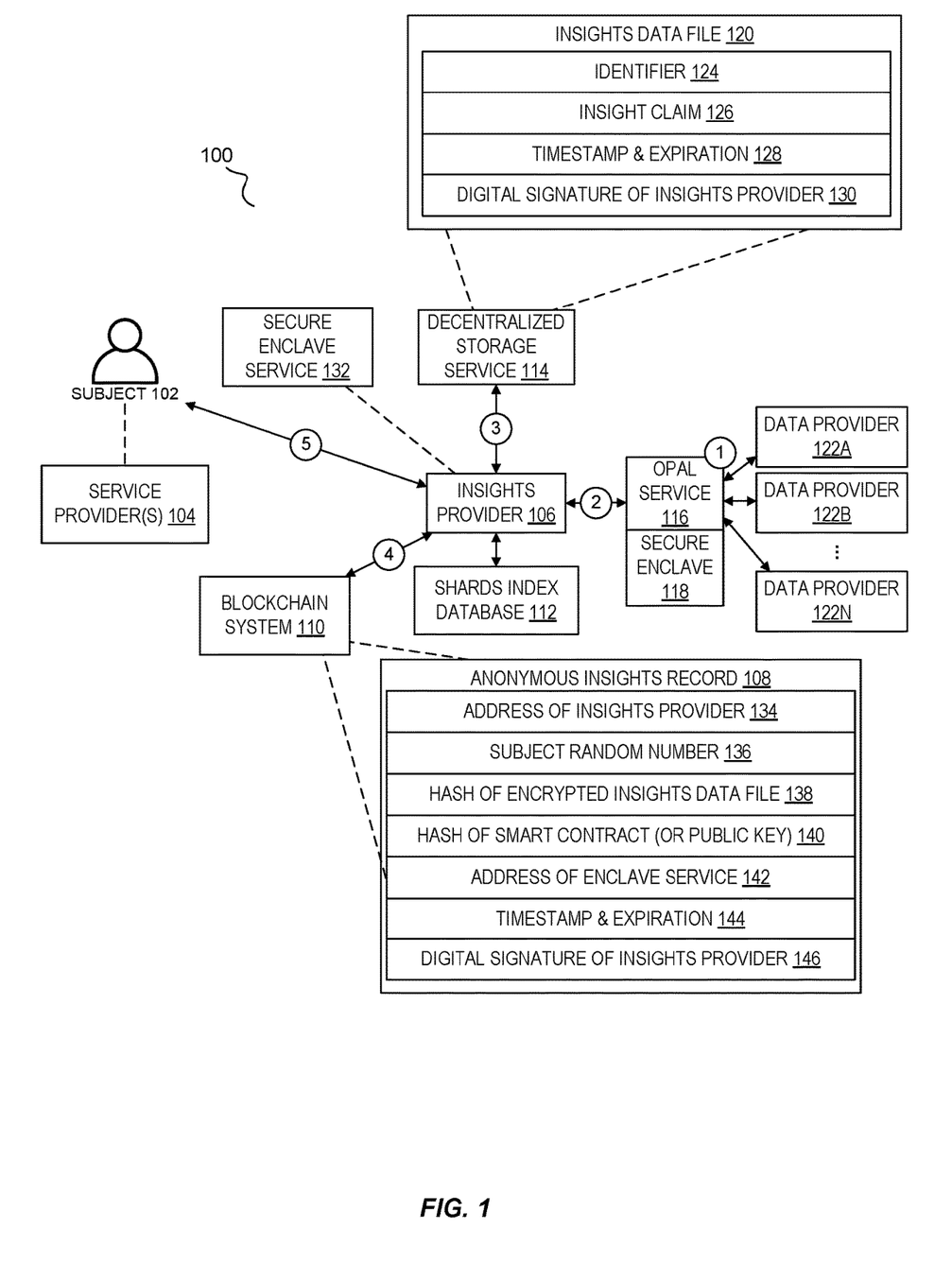
FIG. 1 is a block diagram illustrating an exemplary computing environment in which an insights provider creates an insights data file and anonymous insights record and stores the anonymous insights record on a blockchain according to some examples.

FIG. 1 is a block diagram illustrating an exemplary computing environment 100 in which an insights provider creates an insights data file (or "IDF" or insights data record) and anonymous insights record (or "AIR") and records the anonymous insights record to a blockchain according to some embodiments. As indicated above, when a user (e.g., a subject 102) seeks to obtain services from a service provider 104, the service provider typically desires to obtain trusted insights or claims about the subject to assist the service provider in its analysis of whether to provide the requested services to the subject and on what terms. As described in more detail hereinafter, to enable service providers 104 and other queriers to obtain such insights information in a secure manner, an insights provider 106 creates an anonymous insights record (e.g., an anonymous insights record 108) that is recorded on a blockchain 110 responsive a request from a subject 102 indicating that the user desires to share one or more items of insights information. In some examples, an anonymous insights record 108 contains a single-use (or limited number of use) random number, also referred to herein as a subject random number or "SRN," that is used by the insights provider 106 to index the data in a shards index database 112 (or "SIDB") for the relevant shards of the insights data file. For example, the insights provider 106 can store the insights data file in an encrypted form, where the ciphertext is sharded into multiple segments. These multiple segments can then be stored across multiple separate repositories using a decentralized file storage service 114 (such as, e.g., the InterPlanetary File System (IPFS) used to store the segments across multiple separate internet-connected repositories). The insights provider 106 maintains data indicating a location of each of the shards within a private and secure shards index database 112.

In some examples, a client system used by a subject 102, service provider 104, or other entities (e.g., to access the insights provider 106, secure enclave service 132, blockchain system 110, etc.) can be implemented as a software application running on a client computing device (e.g., a general-purpose personal computer, such as a desktop or laptop computer running a standard operating system, as well as cellular, wireless, and handheld devices running mobile software and capable of supporting a number of networking and messaging protocols) or running as a software application implemented by computing resources (e.g., physical servers, virtual machine (VM) instances, containers, object storage, block-level storage, network-related resources, databases, etc.) located in an on-premises datacenter or on computing resources provided by a cloud provider network. Similarly, the insights provider 106, shards index database 112, OPAL service 116, secure enclave service 132, etc., each can be implemented as application software running on computing resources directly managed by an entity associated with the insights provider 106 or running on computing resources provided by a cloud provider network and which listen and respond to requests from client computer systems. In some examples, computer systems send requests to the insights provider 106 across one or more intermediate networks (e.g., including the public internet), using a message set and communications protocol directed at a predefined application programming interface (API) implemented by the attestation provider. Here, an API refers generally to an interface and/or communication protocol between a client (e.g., a client computer system) and a server (e.g., an attestation provider server), such that a request generated using a predefined format causes the server to generate a response or cause predefined actions to be initiated.

In FIG. 1, the numbered circles (1)-(5) illustrate a process for creating an insights data file (e.g., an insights data file 120) and a corresponding anonymous insights record (e.g., an anonymous insights record 108) and recording the anonymous insights record to a blockchain system 110. In some examples, at circle (1), an Open Algorithms, or "OPAL," service 116 computes insights related to a subject (e.g., a subject 102) using its internal algorithms and a set of data located at one or more data providers (e.g., including data provider 122A, data provider 122B, . . . , data provider 122N). The data providers shown in FIG. 1, for example, can include financial institutions, credit rating agencies, healthcare institutions, government institutions, and the like. The insights can broadly include any information about a subject such as, for example, an age or age range of the subject, an income or income bracket, a gender, a geographic location of the subject, health information, other financial information, etc.

In some examples, the OPAL service 116 optionally performs these computations using a hardware-based trusted execution environment provided by a secure enclave 118. In general, a secure enclave 118 is an isolated compute environment used to protect and securely process sensitive data, including personally identifiable information, financial information, or any other information from which subject insights information may be derived. For example, a secure enclave 118 can include a fully isolated hardware or software based computing system that has been constrained in terms of access to storage and external networking and, in some examples, interactions with a secure enclave 118 involve use of a secure local channel to exchange data.

In some examples, at circle (2), the OPAL service 116 provides one or more insights about the subject generated by the OPAL service to the insights provider 106 using a secure connection. The OPAL service 116 can be managed by an entity that different from an entity that manages the insights provider 106 or, in other examples, the OPAL service 116 and the insights provider 106 can be managed by the same entity.

At circle (3), in some examples, the insights provider 106 creates and stores an insights data file used to store the insights about the subject obtained from the OPAL service 116. In some examples, the insights provider 106 further encrypts the insights data file and shards the encrypted insights data file into N separate shards using a secret sharing protocol. The secret sharing protocol, for example, enables any M pieces of the N shards to be used to reconstruct the encrypted IDF (where M may be less than N). In some examples, the insights provider 106 stores the shards across multiple separate storage locations on the internet using a decentralized file storage service 114 (e.g., using the InterPlanetary File System). The insights provider 106 stores, in a private and secure shards index database 112, identifiers of storage locations at which each of the shards is stored using the decentralized file storage service 114. In other examples, instead of or in addition to using a decentralized storage service 114, the insight provider 106 stores the encrypted insights data file in a secure data store managed by the insights provider 106 or in a data store provided by a cloud provider or other external service accessible to the insights provider 106.

A given subject can be associated with any number of separate insights obtained by the OPAL service 116 from various different data providers. As indicated above, for example, the insights generated by the OPAL service 116 can include insights about any number of different characteristics of a subject 102 including, e.g., an age range, an income range, and so forth. In some examples, the insights provider 106 creates a separate insights data file for each of the separate insights or, in other examples, insights data files can include multiple separate insights about a subject. In some examples, the insights provider 106 can create separate insights data files for a subject by type of insight (e.g., one insights data file for financial related insight claims, another insights data file for healthcare related insight claims, etc.).

In general, the insight claims about a subject 102 can be obtained by the OPAL service 116 at any point in time or responsive to various types of requests to generate the insight claims. For example, a user (e.g., subject 102) might intend to interact with one or more particular types of service provider 104 (e.g., three different home loan providers) and desire to provide particular insights to the providers (e.g., credit history information). In this example, the user might use a computing device to access a web-based portal, mobile application, or other interface provided by the insights provider 106 to request the creation of three separate anonymous insights records and subject random numbers that each of the providers can use to access the identified insights, resulting the OPAL service 116 and insights provider 106 obtaining the requested insights. In other examples, a service provider can initiate a request to obtain particular insights about a subject 102, where the subject provides input approving one or more service provider's request for the data, resulting the creation of one or more anonymous insights records and subject random numbers for the requested insights, as described in more detail hereinafter.

An insights data file can include some or all the following data items: a globally unique identifier 124 of the insights data file, a data item indicating an insight claim 126 about the corresponding subject (e.g., data indicating the subject's age range, indicating the subject's income range, etc.), a timestamp indicating a creation time of the insights data file and an expiration time 128 for the insights data file (e.g., where the insights data file is invalid past the expiration time and is to be deleted from the decentralized storage service 114), and a digital signature of the insights provider 130 as the authoritative issuer of the insights data file. The expiration time associated with each insights data file can depend on the type of the information included in the insights claim, based on a user-specified expiration time, or based on any other condition.

At circle (4), in some examples, once the shards of the encrypted insights data file are successfully stored, the insights provider 106 creates an anonymous insights record (or "AIR") that includes a copy of a subject random number created for the record and a hash of the corresponding encrypted insights data file and stores the anonymous insights record on the blockchain 110. The hash can be used by the insights provider 106 or secure enclave service 118, for example, when the insights data file is later constructed from storage to obtain assurance that the intended insights data file is being processed (e.g., by comparing the hash of the insights data file stored in the anonymous insights record to a hash generated based on a reconstructed copy of the insights data file to ensure that the hashes match).

In some examples, an anonymous insights record 108 further includes some or all the following data items generated by the insights provider 106: an address of a service endpoint of the insights provider 134 (e.g., a URI, network address, or other identifier of a service endpoint that a querier can use at a later point in time to notify the insights provider 106 that the querier is seeking an insight about a subject), a subject random number 136 that is usable only once or a limited number of times (e.g., once a subject random number has been forwarded by the subject to the querier and subsequently used by the querier to access the insight, any subsequent requests using the same subject random number are not honored by the insights provider 106), a cryptographic hash of the encrypted insights data file 138, a hash of a smart contract 140 on the blockchain to be invoked to utilize the anonymous insights record (e.g., depending on the blockchain and smart contract construction, this can include the public key of the smart contract published on the blockchain), an address 142 (e.g., a URI, network address, etc.) of a service endpoint of the secure enclaves service 132 used (and possibly controlled by) the insights provider 106, a timestamp of the creation time of the anonymous insights record and of its expiration 144, and a digital signature 146 of the insights provider 106 as the authoritative issuer of the anonymous insights record on the blockchain 110.

At circle (5), in some examples, once the insights provider 106 confirms that the anonymous insights record is on the ledger of the blockchain, the insights provider 106 provides the subject with a copy of the subject random number stored in the anonymous insights record to be used in the future by the subject (e.g., by displaying the subject random number in a web-based console or mobile application interface, by sending the subject random number to the user in a message or file, or otherwise providing the subject with access to an endpoint or interface at which the subject can use a client computing device to obtain the subject random number). In other examples, the insights provider 106 stores the subject random number in association with an account of the subject as managed by the insights provider 106, where the subject can access the random number via the subject's account.

In some examples, the same insights data file containing one or more insights for a subject can be associated with multiple anonymous insights records on the blockchain, where each anonymous insights record has a different subject random number. Over time, for example, a subject can interact with multiple different types of service providers (e.g., a home loan provider, a credit card provider, etc.) and each separate interaction can result in the creation of a new anonymous insights record for use by the respective service providers. In some examples, the service provider 104 (e.g., the home loan provider, credit card provider, etc.) or other querier does not have direct access to the full insights data file for a subject. Instead, the service provider or querier obtains access to only the insight contained in the insights data file via processing performed by the secure enclave services 132, which provides confidential computing capabilities without disclosing the insights data file to external entities.

Figure 2:
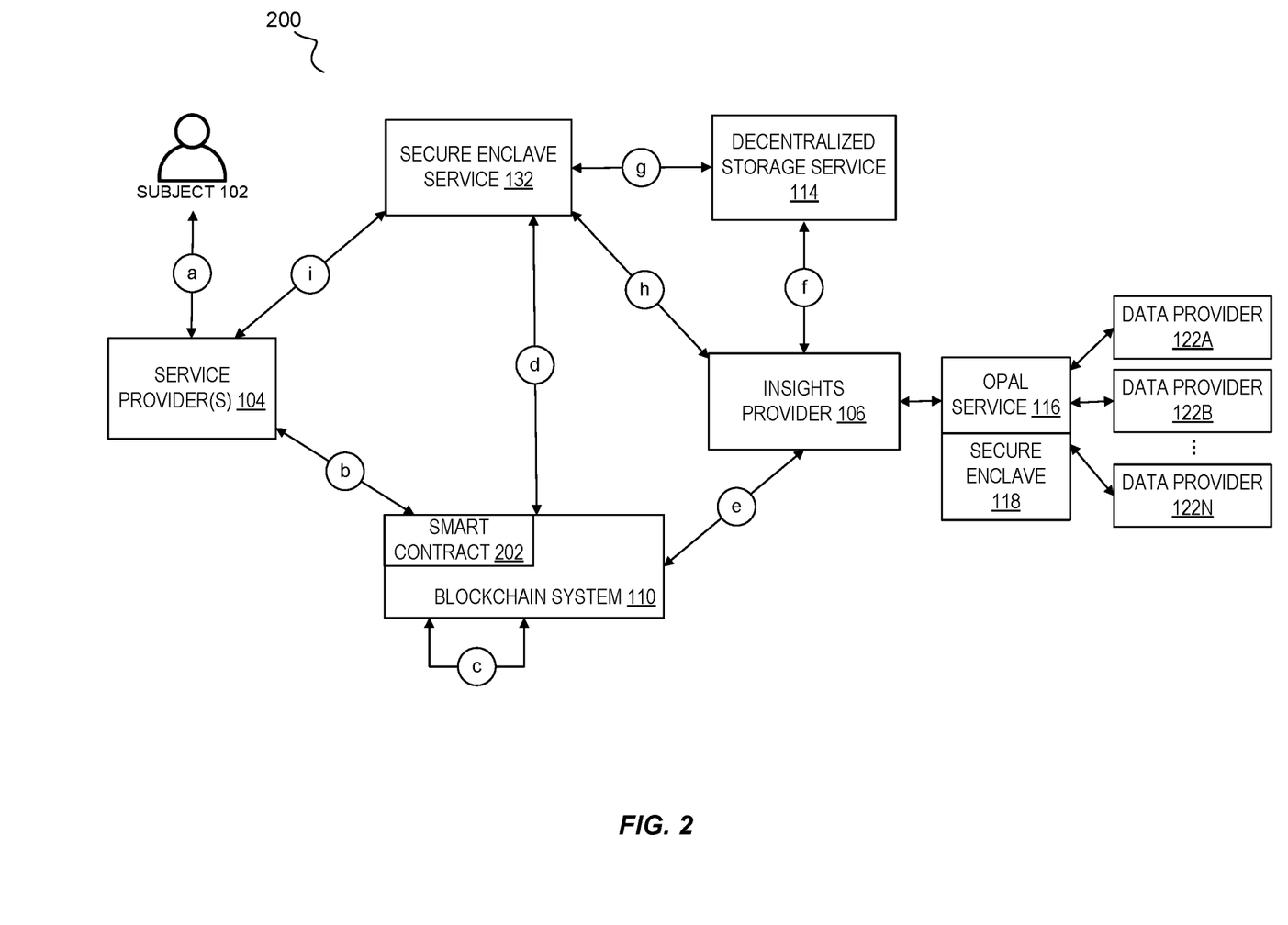
FIG. 2 is a block diagram illustrating an exemplary computing environment in which an insights provider provides access to an insight claim about a subject based on a request identifying a limited-use subject random number according to some examples.

FIG. 2 is a block diagram illustrating an exemplary computing environment in which a insights provider provides access to an insight claim about a subject based on a request identifying a limited-use subject random number according to some examples. In some examples, when a subject 102 requests services from a services provider 104, the subject 102 provides the service provider 104 with a subject random number associated with an insight claim to be used by the service provider 104. For example, as indicated above, a subject 102 might cause the insights provider 106 to create a subject random number to be used to provide limited access to a claim about the subject, such as credit information, income information, etc. A subject, for example, can obtain one or more subject random numbers from the insights provider 106 if the subject intends to interact with one or more service providers, where the subject random numbers provided to the subject are stored by the insights provider 106 in association with a user account of the subject with the insights provider. As indicated, the subject random number enables the service provider to which the subject random number is provided to obtain one or more insight claims about the subject (e.g., insights contained within the insights data file identified by the corresponding anonymous insights record) without accessing the insights data file itself.

In some examples, using the subject random number provided by the subject, the service provider 104 (e.g., as the querier) searches through the confirmed blocks of the ledger of the blockchain 110 to locate an anonymous insights record 108 that includes a matching subject random number. Once a matching anonymous insights record is located, the service provider 104 invokes a smart contract 202 that is identified by the anonymous insights record. In some examples, the smart contract is authored, owned, and controlled by the insights provider 106. A smart contract, for example, is an executable program stored on the blockchain that is invoked when certain conditions are met. The service provider 104 (e.g., the querier) invoking the smart contract 202 provides its own public key as input, thereby leaving irrevocable evidence on the blockchain of the identity of the service provider 104.

In some examples, the smart contract 202 performs several tasks including: 1) recording usage of the subject random number on the blockchain by issuing a transaction on the blockchain that contains the subject random number and the public key (e.g., blockchain address) of the insights provider 106; 2) implicitly signals to the insights provider 106 that a given subject random number has been consumed and that the service provider 104 is ready to interact with the relevant service endpoint at the secure enclaves service 132 to obtain the desired insight claims; and 3) optionally collect payment from the service provider 104 using an available on-chain payment mechanism.

For example, as shown in FIG. 2, at circle (a) the subject 102 provides the service provider 104 with an unused, or otherwise still valid, subject random number to enable the service provider 104 to obtain one or more insights about the subject from the insights provider 106. At circle (b), in some examples, the service provider 104 searches through the blocks of the ledger of the blockchain 110 to locate an anonymous insights record that includes the subject random number provided by the subject 102. Once located, the service provider 104 invokes the smart contract stated in the anonymous insights record and provides the service provider's 104 public key and, optionally, payment.

At circle (c), in some examples, invocation of the smart contract 202 causes the use of the subject random number by the service provider 104 to be recorded in a new transaction on the blockchain 110. In some examples, the record stored to the blockchain 110 evidencing the use of the subject random number includes some or all of: a timestamp indicating when the service provider 104 invoked the smart contract 202 requesting use of the subject random number, the subject random number being used, and an identifier of the service provider 104 (e.g., a public key of the service provider 104). At circle (d), in some examples, the service provider 104 accesses the URI or other address information included in the identified anonymous insights record, which directs the service provider 104 to a service endpoint of the secure enclave service 132. In some examples, the service provider 104 accessing the endpoint authenticates itself with the secure enclave service 132 or insights provider 106 (e.g., using a username and password, preshared key, a digital certificate, or any other authentication mechanism) and further provides the subject random number obtained from the blockchain 110.

In some examples, at circle (e), the insights provider 106 concurrently runs a blockchain client with access to confirmed blocks on the blockchain 110. The blockchain client, for example, can scan for the confirmed blocks on a continuous or largely continuous basis and, in particular, can scan for specific transactions on the blockchain 110 that are addressed to the public key of the insights provider 106. Once the blockchain client of the insights provider 106 identifies a new block on the blockchain with a subject random number originating from a request by a service provider 104, the blockchain client generates and sends a message to the insights provider 106 notifying it that a new request for one or more insight claims (e.g., in a corresponding insights data file) is pending processing.

At circle (f), in some examples, the message received by the insights provider 106 from the blockchain client causes the insights provider to locate and collect the shards of the relevant insights data file referenced in the anonymous insights record on the blockchain identified by the blockchain client. In some examples, at circle (g), the insights provider 106 reconstructs the encrypted insights data file and loads the file into the secure enclave service 132 using a secure communication channel. At circle (h), in some examples, the insights provider 106 also provides its authorization token and the decryption key for the encrypted insights data file into the secure enclave service 132. Within its trusted execution environment, the secure enclave service 132 uses the decryption key to decipher the encrypted insights data file into a plaintext file. At circle (i), in some examples, the secure enclave service 132 provides the insight claims included in the decrypted insights data file to the service provider 104 and deletes the inputs received earlier from its memory. In this manner, the service provider 104 obtains access to the requested insights without direct access to the corresponding insights data file of the subject 102 or other personal data associated with the subject 102.

Figure 3:
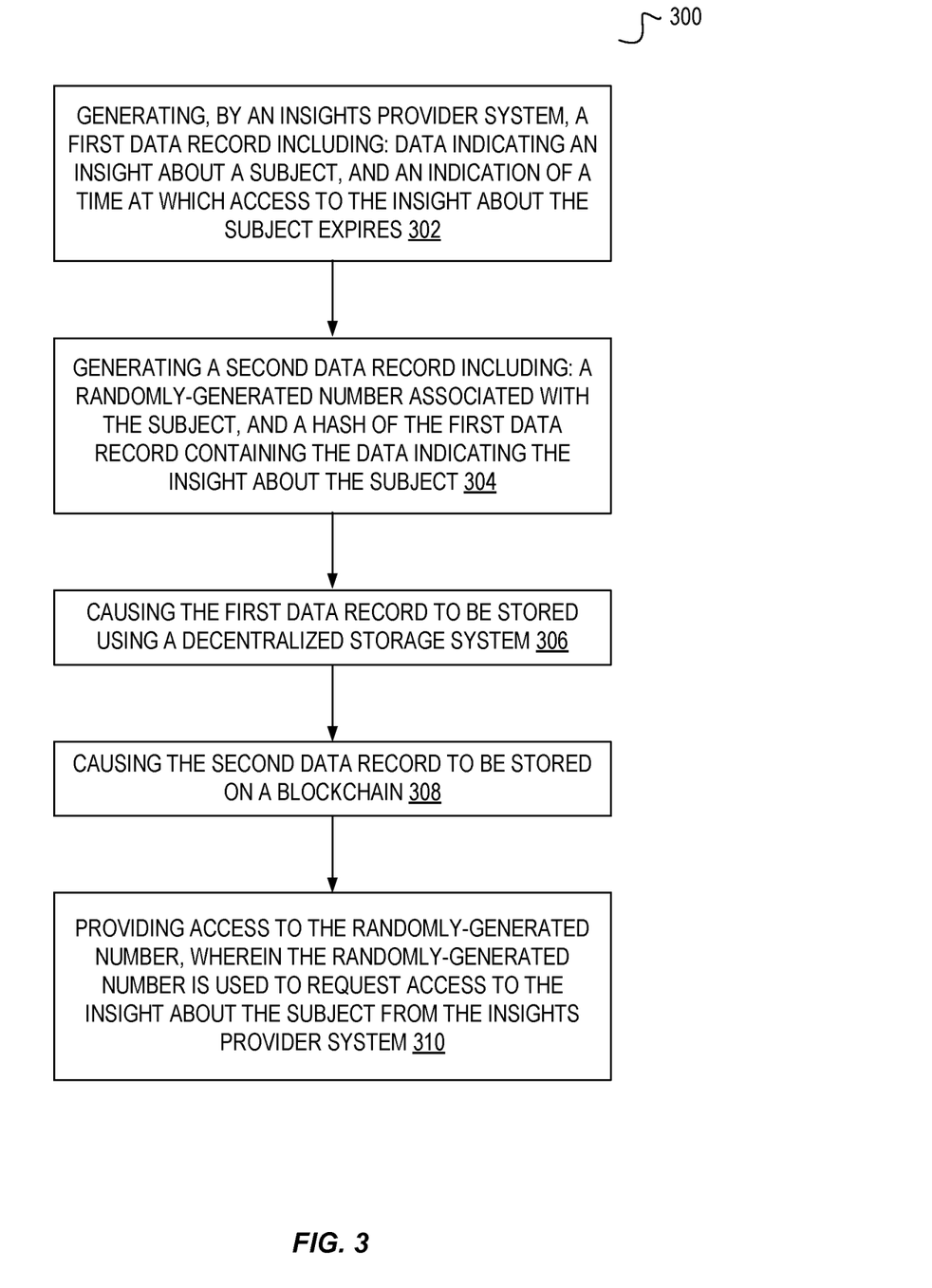
FIG. 3 is a flow diagram illustrating operations for an insights provider to create an insights data file (or record) including an insights claim about a subject and to create an anonymous insights record associated with the insights data record according to some examples.

FIG. 3 is a flow diagram illustrating operations 300 for an insights provider to create an insights data file (or record) including an insights claim about a subject and to create an anonymous insights record associated with the insights data record according to some examples. Some or all of the operations 300 (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations 300 are performed by an insights provider 106 and associated components of the other figures.

In some embodiments, at step 302, the operations include generating, by an insights provider system, a first data record including data indicating an insight about a subject and an indication of a time at which access to the insight about the subject expires.

In some embodiments, at step 304, the operations further include generating a second data record including: a randomly-generated number associated with the subject, and a hash of the first data record containing the data indicating the insight about the subject.

In some embodiments, at step 306, the operations further include causing the first data record to be stored using a decentralized storage system.

In some embodiments, at step 308, the operations further include causing the second data record to be stored on a blockchain.

In some embodiments, at step 310, the operations further include providing access to the randomly-generated number associated with the subject, wherein the randomly-generated number is used to request access to the insight about the subject from the insights provider system.

Figure 4:
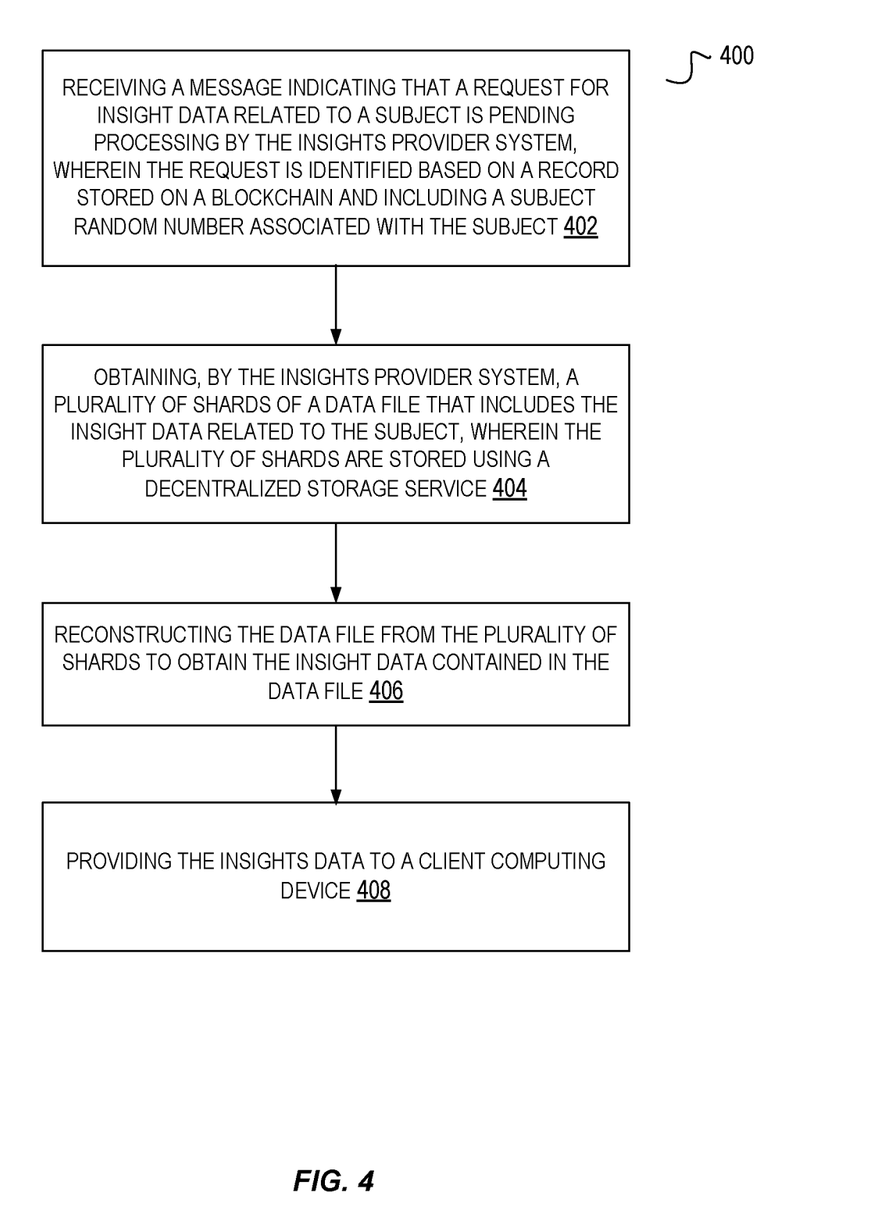
FIG. 4 is a flow diagram illustrating operations for an insights provider to process a request from a service provider or other querier for an insight claim associated with a subject and stored in an insights data file according to some examples.

FIG. 4 is a flow diagram illustrating operations 400 for an insights provider to process a request from a service provider or other querier for an insight claim associated with a subject and stored in an insights data file according to some examples. Some or all of the operations 400 (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations 400 are performed by an insights provider 106 and associated components of the other figures.

In some embodiments, at step 402, the operations include receiving a message indicating that a request for insight data related to a subject is pending processing by the insights provider system, wherein the request is identified based on a record stored on a blockchain and including a subject random number associated with the subject.

In some embodiments, at step 404, the operations further include obtaining, by the insights provider system, a plurality of shards of a data file that includes the insight data related to the subject, wherein the plurality of shards are stored using a decentralized storage service;

In some embodiments, at step 406, the operations further include reconstructing the data file from the plurality of shards to obtain the insight data contained in the data file; and In some embodiments, at step 408, the operations further include providing the insights data to a client computing device.

In some embodiments, the data file is encrypted, and wherein the method further comprises using a secure enclave service to decrypt the data file and provide the insight data to a requesting client device.

In some embodiments, the subject random number is usable a limited number of times.

In some embodiments, the message is received from a client that identifies a record on a blockchain indicating that the request is pending processing, and wherein the record on the blockchain is created based on a client computing device invoking a smart contract associated with a record on the blockchain identifying the subject random number.

In some embodiments, the operations further include generating, by the insights provider system, the data file using a secure enclave to compute the insight data related to the subject, and wherein the insight data is derived from data obtained by the insights provider from at least one data provider.

In some embodiments, the data file includes data indicating a plurality of separate insights related to the subject.

In some embodiments, the operations further include generating, by the insights provider system, the data file including the insight data related to the subject, wherein the data file includes at least one of: an identifier of the data file, the insight data, an expiration time of the data file, and a digital signature of the insights provider; and storing the data file using a decentralized storage service.

In some embodiments, the operations further include generating, by the insights provider system, an anonymous insights record to be stored on the blockchain, wherein the anonymous insights record includes at least one of: the subject random number, a hash of the data file, an identifier of an endpoint of a secure enclave service associated with the insights provider system, an expiration time of the anonymous insights record, and a digital signature of the insights provider; and storing the anonymous insights record on the blockchain.

In some embodiments, a storage location of each of the plurality of shards of the data file is stored in a shards index database managed by the insights provider system, and wherein the storage location of each of the plurality of shards of the data file is indexed in the shards index database by the subject random number.

In some embodiments, the insight data includes at least one of: financial services information related to the subject, healthcare information related to the subject, or demographic information related to the subject.

Implementation Mechanism—Hardware Overview

According to one embodiment, the techniques described herein are implemented by one or more special-purpose computing devices. The special-purpose computing devices may be desktop computer systems, portable computer systems, handheld devices, networking devices or any other device that incorporates hard-wired and/or program logic to implement the techniques. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination thereof. Such special-purpose computing devices may also combine custom hard-wired logic, ASICs, or FPGAs with custom programming to accomplish the techniques.

Figure 5:
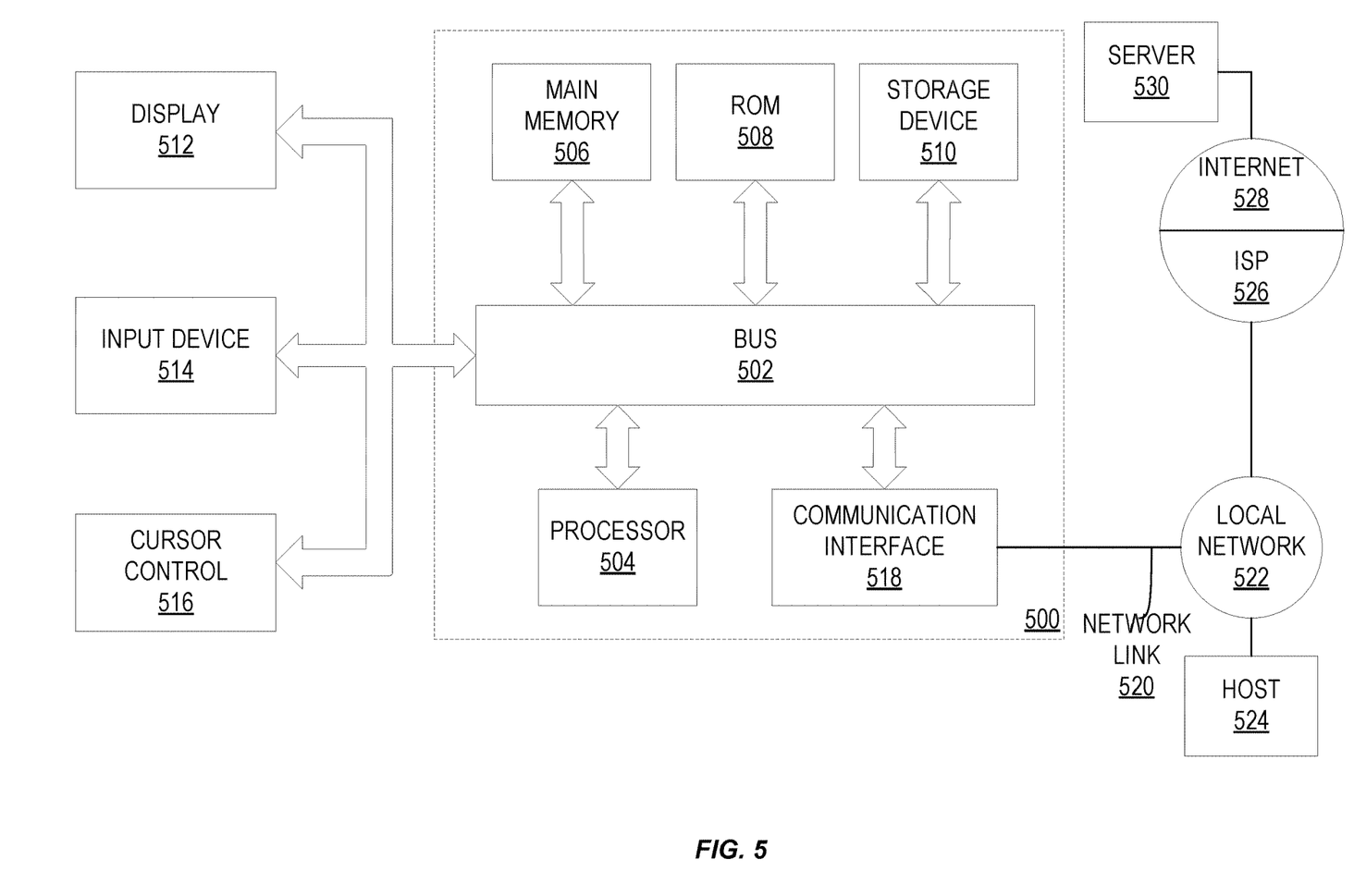
FIG. 5 is a block diagram illustrating an example computer system that may be used in some examples.

FIG. 5 is a block diagram that illustrates a computer system 500 utilized in implementing the above-described techniques, according to an embodiment. Computer system 500 may be, for example, a desktop computing device, laptop computing device, tablet, smartphone, server appliance, computing mainframe, multimedia device, handheld device, networking apparatus, or any other suitable device.

Computer system 500 includes one or more buses 502 or other communication mechanism for communicating information, and one or more hardware processors 504 coupled with buses 502 for processing information. Hardware processors 504 may be, for example, general purpose microprocessors. Buses 502 may include various internal and/or external components, including, without limitation, internal processor or memory busses, a Serial ATA bus, a PCI Express bus, a Universal Serial Bus, a HyperTransport bus, an Infiniband bus, and/or any other suitable wired or wireless communication channel.

Computer system 500 also includes a main memory 506, such as a random access memory (RAM) or other dynamic or volatile storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 a special-purpose machine that is customized to perform the operations specified in the instructions.

Computer system 500 further includes one or more read only memories (ROM) 508 or other static storage devices coupled to bus 502 for storing static information and instructions for processor 504. One or more storage devices 510, such as a solid-state drive (SSD), magnetic disk, optical disk, or other suitable non-volatile storage device, is provided and coupled to bus 502 for storing information and instructions.

Computer system 500 may be coupled via bus 502 to one or more displays 512 for presenting information to a computer user. For instance, computer system 500 may be connected via an High-Definition Multimedia Interface (HDMI) cable or other suitable cabling to a Liquid Crystal Display (LCD) monitor, and/or via a wireless connection such as peer-to-peer Wi-Fi Direct connection to a Light-Emitting Diode (LED) television. Other examples of suitable types of displays 512 may include, without limitation, plasma display devices, projectors, cathode ray tube (CRT) monitors, electronic paper, virtual reality headsets, braille terminal, and/or any other suitable device for outputting information to a computer user. In an embodiment, any suitable type of output device, such as, for instance, an audio speaker or printer, may be utilized instead of a display 512.

One or more input devices 514 are coupled to bus 502 for communicating information and command selections to processor 504. One example of an input device 514 is a keyboard, including alphanumeric and other keys. Another type of user input device 514 is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. Yet other examples of suitable input devices 514 include a touch-screen panel affixed to a display 512, cameras, microphones, accelerometers, motion detectors, and/or other sensors. In an embodiment, a network-based input device 514 may be utilized. In such an embodiment, user input and/or other information or commands may be relayed via routers and/or switches on a Local Area Network (LAN) or other suitable shared network, or via a peer-to-peer network, from the input device 514 to a network link 520 on the computer system 500.

A computer system 500 may implement techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 510. Volatile media includes dynamic memory, such as main memory 506. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or a solid state drive of a remote computer. The remote computer can load the instructions into its dynamic memory and use a modem to send the instructions over a network, such as a cable network or cellular network, as modulate signals. A modem local to computer system 500 can receive the data on the network and demodulate the signal to decode the transmitted instructions. Appropriate circuitry can then place the data on bus 502. Bus 502 carries the data to main memory 506, from which processor 504 retrieves and executes the instructions. The instructions received by main memory 506 may optionally be stored on storage device 510 either before or after execution by processor 504.

A computer system 500 may also include, in an embodiment, one or more communication interfaces 518 coupled to bus 502. A communication interface 518 provides a data communication coupling, typically two-way, to a network link 520 that is connected to a local network 522. For example, a communication interface 518 may be an integrated services digital network (ISDN) card, cable modem, satellite modem, or a modem to provide a data communication connection to a corresponding type of telephone line. As another example, the one or more communication interfaces 518 may include a local area network (LAN) card to provide a data communication connection to a compatible LAN. As yet another example, the one or more communication interfaces 518 may include a wireless network interface controller, such as a 802.11-based controller, Bluetooth controller, Long Term Evolution (LTE) modem, and/or other types of wireless interfaces. In any such implementation, communication interface 518 sends and receives electrical, electromagnetic, or optical signals that carry digital data streams representing various types of information.

Network link 520 typically provides data communication through one or more networks to other data devices. For example, network link 520 may provide a connection through local network 522 to a host computer 524 or to data equipment operated by a Service Provider 526. Service Provider 526, which may for example be an Internet Service Provider (ISP), in turn provides data communication services through a wide area network, such as the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

In an embodiment, computer system 500 can send messages and receive data, including program code and/or other types of instructions, through the network(s), network link 520, and communication interface 518. In the Internet example, a server 530 might transmit a requested code for an application program through Internet 528, ISP 526, local network 522 and communication interface 518. The received code may be executed by processor 504 as it is received, and/or stored in storage device 510, or other non-volatile storage for later execution. As another example, information received via a network link 520 may be interpreted and/or processed by a software component of the computer system 500, such as a web browser, application, or server, which in turn issues instructions based thereon to a processor 504, possibly via an operating system and/or other intermediate layers of software components.

In an embodiment, some or all of the systems described herein may be or comprise server computer systems, including one or more computer systems 500 that collectively implement various components of the system as a set of server-side processes. The server computer systems may include web server, application server, database server, and/or other conventional server components that certain above-described components utilize to provide the described functionality. The server computer systems may receive network-based communications comprising input data from any of a variety of sources, including without limitation user-operated client computing devices such as desktop computers, tablets, or smartphones, remote sensing devices, and/or other server computer systems.

In an embodiment, certain server components may be implemented in full or in part using "cloud"-based components that are coupled to the systems by one or more networks, such as the Internet. The cloud-based components may expose interfaces by which they provide processing, storage, software, and/or other resources to other components of the systems. In an embodiment, the cloud-based components may be implemented by third-party entities, on behalf of another entity for whom the components are deployed. In other embodiments, however, the described systems may be implemented entirely by computer systems owned and operated by a single entity.

In an embodiment, an apparatus comprises a processor and is configured to perform any of the foregoing methods. In an embodiment, a non-transitory computer readable storage medium, storing software instructions, which when executed by one or more processors cause performance of any of the foregoing methods.

EXTENSIONS AND ALTERNATIVES

As used herein, the terms "first," "second," "certain," and "particular" are used as naming conventions to distinguish queries, plans, representations, steps, objects, devices, or other items from each other, so that these items may be referenced after they have been introduced. Unless otherwise specified herein, the use of these terms does not imply an ordering, timing, or any other characteristic of the referenced items.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. In this regard, although specific claim dependencies are set out in the claims of this application, it is to be noted that the features of the dependent claims of this application may be combined as appropriate with the features of other dependent claims and with the features of the independent claims of this application, and not merely according to the specific dependencies recited in the set of claims. Moreover, although separate embodiments are discussed herein, any combination of embodiments and/or partial embodiments discussed herein may be combined to form further embodiments.

Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A computer-implemented method performed by an insights provider system, the method comprising:
    receiving a message indicating that a request for insight data related to a subject is pending processing by the insights provider system, wherein the request is identified based on a record stored on a blockchain, wherein the record stored on the blockchain includes a subject random number associated with the subject, and wherein the record indicates a number of times the subject random number has been used;
    responsive to determining, by the insights provider system, that the number of times the subject random number has been used is not more than a maximum permitted number of times the subject random number can be used:
        identifying, based on the subject random number, storage locations of a plurality of shards of a data file that includes the insight data related to the subject, wherein the plurality of shards are stored using a decentralized storage service;
        obtaining, by the insights provider system, the plurality of shards of the data file that includes the insight data related to the subject;
        reconstructing the data file from the plurality of shards to obtain the insight data contained in the data file; and
        providing the insights data to a client computing device.

2. The computer-implemented method of claim 1, wherein the data file is encrypted, and wherein the method further comprises using a secure enclave service to decrypt the data file and provide the insight data to a requesting client device.

3. The computer-implemented method of claim 1, wherein the subject random number is a first subject random number, and wherein the subject is further associated with a second subject random number associated with the data file that includes the insight data related to the subject.

4. The computer-implemented method of claim 1, wherein the message is received from a client that identifies a record on a blockchain indicating that the request is pending processing, and wherein the record on the blockchain is created based on a client computing device invoking a smart contract associated with a record on the blockchain identifying the subject random number.

5. The computer-implemented method of claim 1, further comprising generating, by the insights provider system, the data file using a secure enclave to compute the insight data related to the subject, and wherein the insight data is derived from data obtained by the insights provider system from at least one data provider.

6. The computer-implemented method of claim 1, wherein the data file includes data indicating a plurality of separate insights related to the subject.

7. The computer-implemented method of claim 1, further comprising:
    generating, by the insights provider system, the data file including the insight data related to the subject, wherein the data file includes at least one of: an identifier of the data file, the insight data, an expiration time of the data file, and a digital signature of the insights provider system; and
    storing the data file using a decentralized storage service.

8. The computer-implemented method of claim 1, further comprising:
    generating, by the insights provider system, an anonymous insights record to be stored on the blockchain, wherein the anonymous insights record includes at least one of: the subject random number, a hash of the data file, an identifier of an endpoint of a secure enclave service associated with the insights provider system, an expiration time of the anonymous insights record, and a digital signature of the insights provider system; and
    storing the anonymous insights record on the blockchain.

9. The computer-implemented method of claim 1, wherein a storage location of each of the plurality of shards of the data file is stored in a shards index database managed by the insights provider system, and wherein the storage location of each of the plurality of shards of the data file is indexed in the shards index database by the subject random number.

10. The computer-implemented method of claim 1, wherein the insight data includes at least one of: financial services information related to the subject, healthcare information related to the subject, or demographic information related to the subject.

11. A system comprising:
an insights provider system implemented by a first one or more electronic devices comprising a processor, the insights provider system including instructions that upon execution cause the insights provider system to:
receive a message indicating that a request for insight data related to a subject is pending processing by the insights provider system, wherein the request is identified based on a record stored on a blockchain, wherein the record stored on the blockchain includes a subject random number associated with the subject, and wherein the record indicates a number of times the subject random number has been used,
responsive to determining, by the insights provider system, that the number of times the subject random number has been used is not more than a maximum permitted number of times the subject random number can be used:
identify, based on the subject random number, storage locations of a plurality of shards of a data file that includes the insight data related to the subject, wherein the plurality of shards are stored using a decentralized storage service;
obtain, by the insights provider system, the plurality of shards of the data file that includes the insight data related to the subject,
reconstruct the data file from the plurality of shards to obtain the insight data contained in the data file, and
provide the insights data to a client computing device; and
a client computing device implemented by a second one or more electronic devices comprising a processor, the client computing device including instructions that upon execution cause the client computing device to:
generate the request for insight data related to the subject by invoking a smart contract on a blockchain, wherein the smart contract is associated with a record on the blockchain including the subject random number.

12. The system of claim 11, wherein the data file is encrypted, and wherein the instructions upon execution further cause the insights provider system to use a secure enclave service to decrypt the data file and provide the insight data to a requesting client device.

13. The system of claim 11, wherein the subject random number is a first subject random number, and wherein the subject is further associated with a second subject random number associated with the data file that includes the insight data related to the subject.

14. The system of claim 11, wherein the message is received from a client that identifies a record on a blockchain indicating that the request is pending processing, and wherein the record on the blockchain is created based on a client computing device invoking a smart contract associated with a record on the blockchain identifying the subject random number.

15. The system of claim 11, wherein the instructions upon execution further cause the insights provider system to generate the data file using a secure enclave to compute the insight data related to the subject, and wherein the insight data is derived from data obtained by the insights provider system from at least one data provider.

16. The system of claim 11, wherein the data file includes data indicating a plurality of separate insights related to the subject.

17. The system of claim 11, wherein the instructions upon execution further cause the insights provider system to:
generate, by the insights provider system, the data file including the insight data related to the subject, wherein the data file includes at least one of: an identifier of the data file, the insight data, an expiration time of the data file, and a digital signature of the insights provider system; and
store the data file using a decentralized storage service.

18. The system of claim 11, wherein the instructions upon execution further cause the insights provider system to:
generate an anonymous insights record to be stored on the blockchain, wherein the anonymous insights record includes at least one of: the subject random number, a hash of the data file, an identifier of an endpoint of a secure enclave service associated with the insights provider system, an expiration time of the anonymous insights record, and a digital signature of the insights provider system; and
store the anonymous insights record on the blockchain.

19. The system of claim 11, wherein a storage location of each of the plurality of shards of the data file is stored in a shards index database managed by the insights provider system, and wherein the storage location of each of the plurality of shards of the data file is indexed in the shards index database by the subject random number.

20. The system of claim 11, wherein the insight data includes at least one of: financial services information related to the subject, healthcare information related to the subject, or demographic information related to the subject.

* * * * *